United States Patent [19]

Kopfer et al.

[11] Patent Number: 4,619,651

[45] Date of Patent: Oct. 28, 1986

[54] ANTI-AEROSOLING DRUG RECONSTITUTION DEVICE

[76] Inventors: Rudolph J. Kopfer, 1321 S. Eliseo Dr., Suite 1, Greenbrae, Calif. 94904; Robert E. Smith, Smith Goggles, P.O. Box 2999, Ketchum, Id. 83340

[21] Appl. No.: 644,449

[22] Filed: Aug. 27, 1984

Related U.S. Application Data

[63] Continuation-in-part of Ser. No. 600,504, Apr. 16, 1984.

[51] Int. Cl.[4] .............................................. A61M 5/00

[52] U.S. Cl. ...................................... 604/415; 604/87; 604/414

[58] Field of Search ....................... 604/56, 80, 82–83, 604/87–88, 92, 125, 201, 407–408, 410, 413–416; 141/25–28, 2, 19, 329–330, 369–370, 372, 375, 285–286, 383–386

[56] References Cited

U.S. PATENT DOCUMENTS

| | | | |
|---|---|---|---|
| 2,880,723 | 4/1959 | Adams . | |
| 3,336,924 | 8/1967 | Sarnoff et al. . | |
| 3,375,825 | 4/1968 | Keller . | |
| 3,397,694 | 8/1968 | Ogle . | |
| 3,416,657 | 12/1968 | Sorensen, Jr. . | |
| 3,563,373 | 2/1971 | Paulson . | |
| 3,659,602 | 2/1972 | Cloyd . | |
| 3,826,260 | 7/1974 | Killinger . | |
| 3,826,261 | 7/1974 | Killinger . | |
| 3,872,867 | 3/1975 | Killinger . | |
| 3,995,630 | 12/1976 | van de Veerdonk . | |
| 4,031,895 | 6/1977 | Porter . | |
| 4,121,585 | 10/1978 | Becker, Jr. | 604/86 |
| 4,133,441 | 1/1979 | Mittleman et al. | 604/86 |
| 4,180,070 | 12/1979 | Genese . | |
| 4,328,802 | 5/1982 | Curley et al. . | |
| 4,516,967 | 5/1985 | Kopfer | 604/87 |

*Primary Examiner*—C. Fred Rosenbaum
*Assistant Examiner*—Michelle N. Lester
*Attorney, Agent, or Firm*—Wood, Dalton, Phillips, Mason & Rowe

[57] ABSTRACT

The present invention comprehends the provision of a fluid tight holding chamber which accumulates solution (1) from the vial that aspirates or is pressured out of the vial upon extraction of the cannula from the vial or (2) is aspirated from the syringe before the cannula is removed from the holding chamber. The holding chamber is defined in the neck of the vial by an insert. The insert may be one piece or two piece and has an inner end sealing the contents of the vial from the holding chamber and an outer end sealing the aspirated medicament in the holding chamber. The insert has a luer seal for sealing against the luer connector on the syringe during the practice of certain procedures.

20 Claims, 21 Drawing Figures

ANTI-AEROSOLING DRUG RECONSTITUTION DEVICE

CROSS REFERENCE

This application is a continuation-in-part of Ser. No. 600,504, filed Apr. 16, 1984, entitled "Anti-Aerosoling Drug Reconstitution Device".

BACKGROUND OF THE INVENTION

1. Field of the Invention

This invention relates to a syringe system for combining two dissimilar medicaments and, more particularly, to a structure for shielding a user of the syringe against aspirating or aerosoling solution upon withdrawal of the syringe cannula from a mixing vial.

2. Background Art

It is known to reconstitute drugs by combining and mixing isolated, dissimilar medicaments immediately prior to patient infusion. This procedure is common with drugs that are unstable or deteriorate in solution. By isolating the ingredients, whether two liquids or a liquid and solid, the storage life of the drug can be extended.

Normally a sterilized, evacuated dose vial contains a crystalline component and is hermetically sealed by a pierceable septum. The syringe cannula penetrates the septum to establish communication between the vial chamber and the inside of the syringe barrel. The barrel retains a complementary diluent which is injected into the vial. The vial containing the two components is agitated to completely dissolve the solid. The reconstituted solution is drawn back into the syringe barrel for administration to a patient.

The problem which the present invention obviates arises during the mixing of the isolated medicaments. Complete evacuation of the vial before injection of the diluent is seldom realized. There is thus a residual pressure in the vial after the solution dose is extracted. This residual pressure often causes discharge of some of the remaining solution in the vial through the rupture in the septum made by the cannula. Where the drug is toxic, as is common in oncological treatments, or is otherwise dangerous, this escaping solution may pose a health hazard to persons preparing, administering and receiving the injection.

Protective shields associated with the vial to limit exposure to the solution during admixture are known. In the structure depicted in U.S. Pat. No. 3,336,924 to Sarnoff et al, cooperating cover parts encase the vial and define a chamber to closely, guidingly accept the syringe barrel. A seal between the barrel and cover is effected with the syringe fully seated. Upon partial withdrawal of the cannula from the vial, the medicament freely aspirates into the cover chamber and is confined by the leading edge of the barrel. With the syringe separated from the cover, the medicament is unrestrained, escapes through the chamber opening, which is as large as the barrel diameter, and poses a potential hazard to the syringe operator and/or the person disposing of the used, covered vial.

Another structure that exemplifies the state of the art is described in U.S. Pat. No. 3,659,602, to Cloyd. Cloyd discloses a two component syringe with separate vials penetrable by a double-ended cannula. An adapter sleeve is associated with one of the vials and defines a socket which accepts the end of a stopper piston. To operate the syringe, the vial and sleeve are advanced axially towards each other until the vial bottoms in the socket, thus eliminating the socket. Upon unseating the Luer taper from the adapter sleeve, the sleeve passage is open to the atmosphere. One contends in Cloyd with essentially the same problems associated with the Sarnoff et al structure previously described.

Another problem that the prior art structures make no provision for arises after filling the syringe. During aspiration of the solution from the vial into the barrel, air bubbles may become entrained in the solution. Before infusion, it is common to discharge a small volume of the solution to expel the bubbles. With the prior structures, this generally takes place with the cannula exposed to the environment and subjects the user once again to possible solution exposure.

Expulsion of the drug with the entrained air into the syringe cover in Sarnoff et al, while temporarily shielding the user, accumulates additional solution in the syringe cover in addition to that aspirating from the vial. Escape of the solution from the syringe cover is unobstructed so that once again the user and/or the person subsequently disposing of the vial and cover are liable to come into contact with the solution.

The present invention is specifically directed to overcoming one or more of the above enumerated problems known in the prior structures.

SUMMARY OF THE INVENTION

The present invention comprehends the provision of a fluid tight holding chamber which accumulates solution from the vial that aspirates or is pressured out of the vial upon extraction of the cannula from the vial or any time during the procedure of reconstitution. The chamber is defined in conjunction with the vial septum by a shield cap that surrounds the neck of the vial. The shield cap defines a guide for the needle hub and Luer lock sleeve on the leading portion of the syringe and directs the cannula through a sealing member, the holding chamber, the septum and into the vial.

It is the principal objective of the present invention to provide a simple package that facilitates mixture of dissimilar medicaments and, which traps medicament solution that aspirates from the vial upon insertion or removal of the cannula to shield both a user during admixture and persons subsequently handling the vial package for disposal.

To accomplish this end, the shield cap and vial neck make fluid tight engagement. The shield cap has a penetrable wall portion to admit the cannula. A sealing member lies in the cannula path in the shield cap and is self-sealing to confine the medicament in the holding chamber after the syringe is withdrawn.

The holding chamber can additionally be used to receive the expelled solution with entrained air bubbles before infusion. By partially backing out the syringe, the cannula provides a communication conduit between the holding chamber and the barrel reservoir. The discharged solution is captured in the chamber so that it does not pose an external health hazard.

To consistently seat the Luer lock sleeve and to direct the cannula through the vial septum, a guide cavity is provided at the syringe-receiving end of the shield cap. The guide cavity guides the needle and needle hub so that shield cap and syringe are self-aligning.

It is another aspect of the invention to provide an improved sealing structure between the shield cap and the vial neck. The shield cap has a mating cylindrical portion with an imperforate ring at its free end and a radially inwardly projecting annular rib associated with the ring. The cylindrical portion is slit axially from the ring to permit lengthwise compression of the cylindrical portion to allow for sufficient radial expansion to pass the rib over an enlarged rim on the neck of the vial bottle. With the rib seated behind the rim, a compression ring is disposed over the cylindrical portion to compress the rib radially inwardly to bear the same against the vial. Removal of the shield cap is prohibited with the compression ring in place. The compressed annular rib causes a redundant fluid tight seal to be effected between the shield cap and the vial. In one form of the invention the compression ring interengages with one way notches to prevent removal of the ring and therefore to prevent removal of the vial from the shield cap. Other methods of sealing structure may be effective but the end result is the same.

In an alternative embodiment of the invention the vial itself is used to define at least a portion of the safety holding chamber in which aspirating fluid is contained. An insert is extended into an opening in the neck of the vial and is held in place as by a deformable thin metal cap. The resulting package comprising the vial and insert functions in a comparable manner to the vial with the associated shield cap in the prior system and the advantages attendant the prior system are realized. To most effectively utilize the insert, it is preferred that a vial with an extended neck be employed and the insert be related dimensionally so that substantially the entire holding chamber is defined in the neck. The insert can be closely conformed to and frictionally retained within the neck.

It is also contemplated that a luer seat can be integrally constructed with one of the pieces making up the insert.

To effect the reconstitution, it is necessary for one only to remove a sterile covering from the package and to penetrate the insert with the syringe cannular to establish communication between the syringe barrel and the inside of the vial.

DETAILED DESCRIPTION OF DRAWINGS

Figures 1, 2:
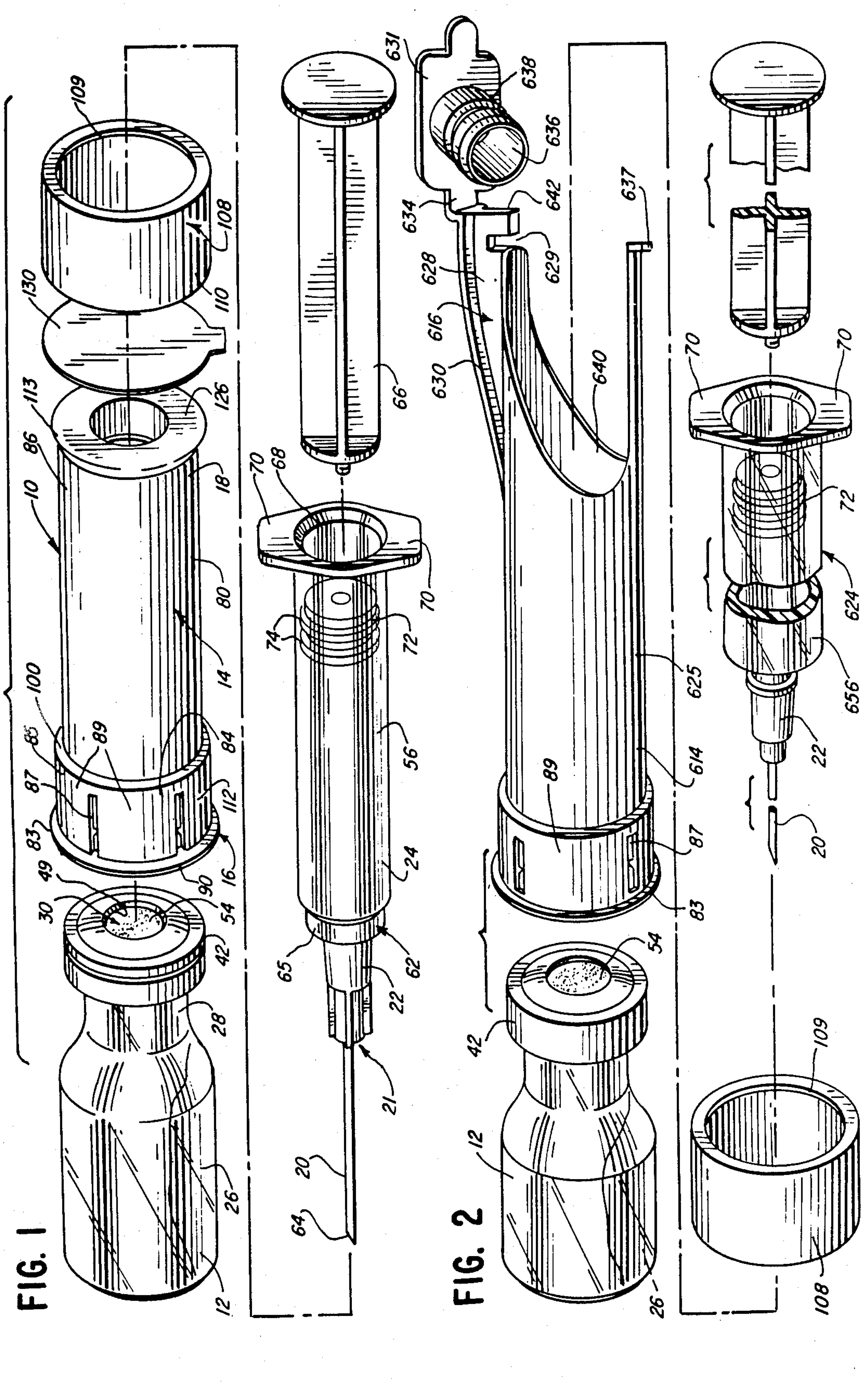
FIG. 1 is an exploded perspective view of a conventional vial operatively associated with a first type of shield cap according to the present invention.
FIG. 2 is an exploded perspective view of a conventional vial operatively associated with a second type of shield cap according to the present invention.
Figures 3, 4, 5:
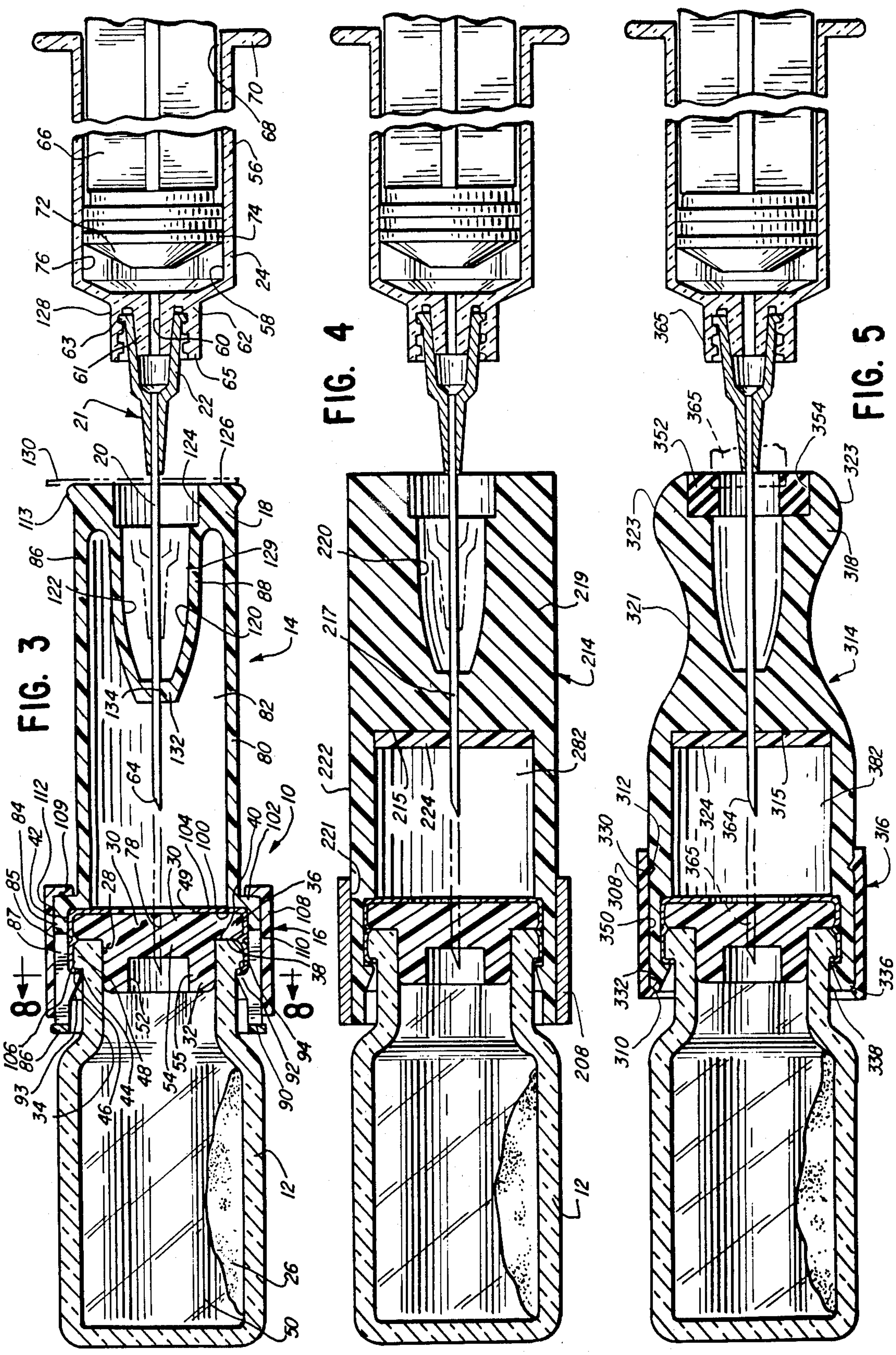
FIG. 3 is a sectional view of the vial, shield cap and syringe of FIG. 1 only in assembled condition with the syringe needle partially inserted into the shield cap.
FIG. 4 is a sectional view similar to that in FIG. 3 with a third type of shield cap according to the present invention.
FIG. 5 is a sectional view as in FIGS. 3 and 4 with a fourth type of shield cap according to the present invention.

FIGS. 1 and 3 illustrate a system embodying the present invention and comprises generally a vial package 10 comprising a glass dose vial 12 and a shield cap at 14 united with the vial 12 through a telescoped connection at 16. The syringe end 18 of the shield cap is adapted to accept a cannula 20 of a needle 21 and a Luer taper on the cannula hub 22 at the leading portion of a conventional syringe 24.

Throughout the description of the invention, like reference numerals will be used to identify the vial 12 and syringe 24 which are conventional in construction and identical in each of FIGS. 1–8, 11 and 12. The modifications to the vial package 10 comprehended by the invention, focus on the shield cap 14.

Before the invention can be appreciated, the basic vial and syringe structures will be described as well as the mixing operation for which the invention is particularly suitable.

The vial 12, which is generally made from glass, is sterilized and contains a measured supply of solid form medicament 26. The open end 28 of the vial is sealed by a resilient stopper 30 having a body 32 that is squeezed into the cylindrical neck opening 34. The body 32 has an integral, enlarged top 36 defining a shoulder 38 sealingly abutting the free edge 40 of the vial 12.

A thin, deformable metal seal 42 surrounds the top 36 and an enlarged rim 48 on the neck 34 of the vial and is crimped to deflect its free edge 44 behind a shoulder 46 defined by the rim 48. The seal 42, as it is crimped, compressibly draws the top 36 against the vial to hermetically seal the vial chamber 50. The cap has a circular cutout 49 to permit access to the stopper by the needle cannula as described below.

The stopper 30 has a cylindrical cavity 52 which establishes communication between the barrel of the syringe 24 and the vial before full penetration by the cannula. The cavity reduces the axial dimension of the septum at the central portion of the stopper 30 to facilitate penetration by the cannula, and also reduces the thickness of annular wall 55 so that it is more readily deformable upon insertion of the stopper 30 into the vial.

Briefly, the syringe 24 is conventional and comprises a barrel 56 defining an internal, liquid retaining reservoir 58 which communicates with the needle 21 through a capillary 60 in a Luer-tapered tip 61 of a Luer-lock type connector 62. The needle 21 has the cannula 20 seated at one end in a female Luer-tapered hub 22 which hub has a locking flange 63 for locking in the sleeve 65 of connector 62. The cannula 20 has a tapered penetrating tip 64.

To effect discharge of liquid through the barrel, a plunger 66 is depressed from the open end 68 of the barrel, toward the cannula. This is accomplished by grasping finger flange 70 with the index and middle fingers, situating the thumb on a rest (not shown) at the end of the plunger and drawing the thumb towards the fingers. A rubber piston or stopper 72 is fit at the end of the plunger and is suitably attached to follow the plunger movement. The stopper 72 has annular rib 74 which closely sealingly conform to the inside surface 76 of the barrel 56. As the plunger is depressed, the stopper compresses the liquid in the reservoir, forcing the discharge of the solution through the cannula 20.

According to the prior art, to carry out the mixing operation, a measured supply of liquid solvent is drawn into the barrel 56. In the alternative, the syringe may be prefilled and packaged in a sterile container. The syringe is advanced toward the vial so that the cannula pierces the septum 54 and establishes communication with the vial chamber 50 which contains the solid component. The liquid supply is then injected by depressing the plunger and the vial shaken to dissolve the powder. The reconstituted solution is extracted by withdrawing the plunger.

Reasonably complete evacuation of the vial before sealing is striven for. However, in practice, only partial evacuation is achieved. Upon injection of the liquid component from the syringe, pressure is developed in the vial. A residual pressure is often maintained after the withdrawal of the fluid into the syringe, and is significant particularly when less than the entire amount of solution is withdrawn from the vial. The residual pressure can cause a discharge of the solution through the rupture 78 in the stopper made by the insertion of the cannula, particularly as the cannula is being withdrawn from the stopper. The solution may be expelled until the pressure in the vial is reduced sufficiently that the self-sealing nature of the stopper obstructs its passage.

The present invention is primarily directed to capturing the solution aspirating from the vial during and after withdrawal of the cannula from the stopper. The shield cap 14 disclosed in FIG. 1 comprises a cylindrical body 80 defining an internal holding chamber 82 with a vial end 84 and syringe end 86.

The vial end 84 of the shield cap 14 has an enlarged diameter connecting portion 85 that is open to accept the neck of the vial. The connecting portion has slits 87 extending axially from a continuous collar 83 at the free edge 90 to a point spaced axially from the internal shoulder 100 forming the junction between the connecting portion 85 and the body 80 of the shield cap 14. The slits 87 divide the connecting portion into plural segments 89, FIGS. 1 and 8. Spaced axially of the collar 83 and projecting radially inwardly from the wall of each segment 89 is a rib 92, which rib is annular with the exception of the breaks caused by the slits 87. The rib 92 has a ramp surface 93 which constricts the opening in the connecting portion and defines a shoulder 94 facing toward the syringe end of the cap at the radially thickest portion of the rib 92.

Figures 6, 7, 8, 9, 10:
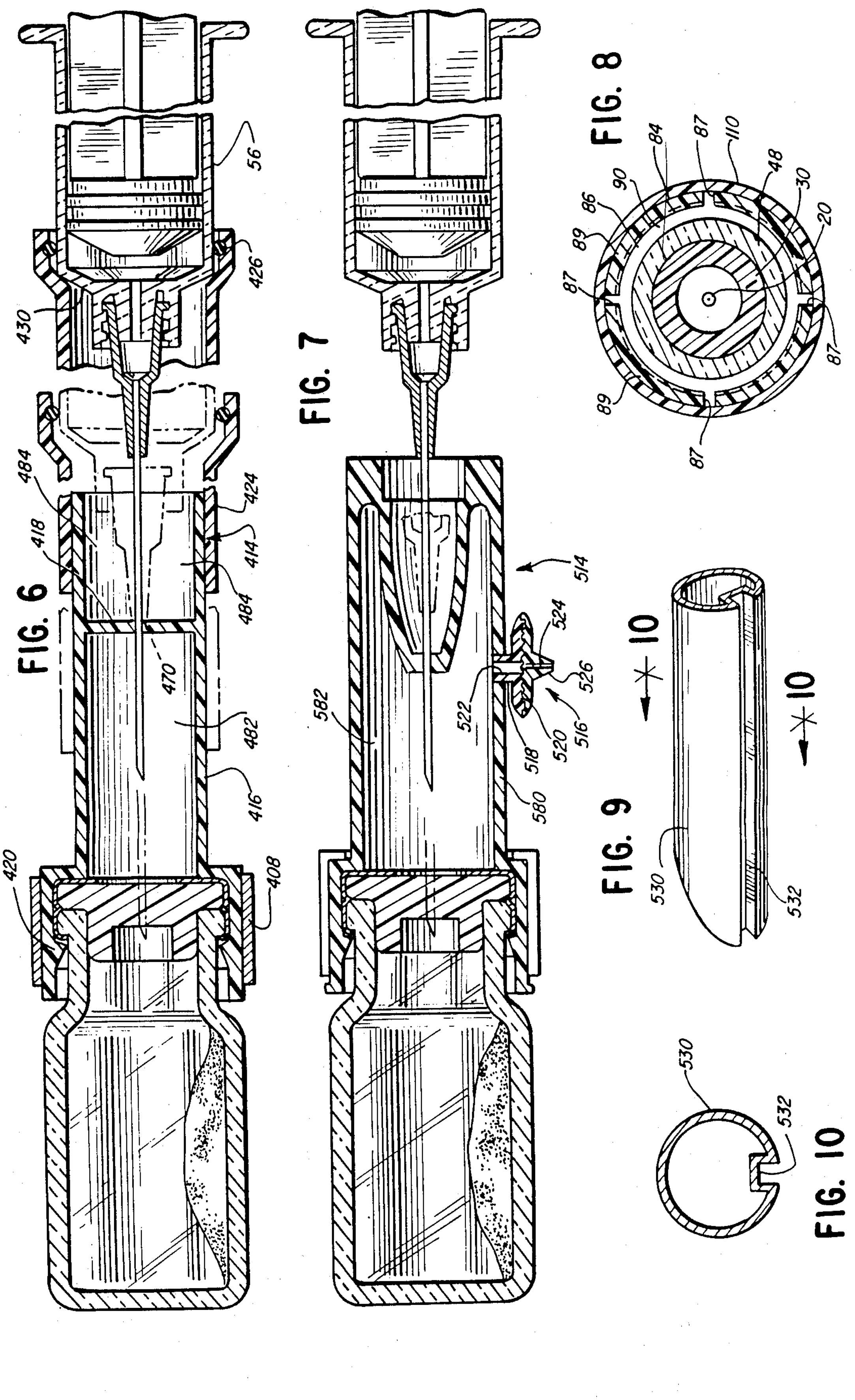
FIG. 6 is a sectional view similar to that in FIGS. 3–5 with a fifth type of shield cap according to the present invention.
FIG. 7 is a sectional view similar to that in FIGS. 3–6 with a sixth type of shield cap according to the present invention.
FIG. 8 is a sectional view of the connection between the vial and the shield cap along line 8—8 of FIG. 3.
FIG. 9 is an enlarged, fragmentary perspective view of a modified form of syringe needle for use with the shield cap of the type shown in FIG. 7.
FIG. 10 is a sectional view of the needle along line 10—10 of FIG. 9.

To assemble the shield cap 14 and vial 12, the connecting portion 85 of the cap and the stopper end of the vial are axially aligned and advanced, one toward the other. The seal 42 about the vial neck is closely surrounded first by the collar 83 of the connecting portion 85. As the connecting portion is advanced toward the vial, the ramp surface 93 on the rib 92 encounters the metal seal and is deflected along with the segments 89 radially outwardly sufficiently to allow passage of the rib. To facilitate this expansion and also the sealing as hereafter described, the plurality of slits 87 between the segments 89, as seen most clearly in FIGS. 1 and 8, are provided. The slits 87 end short of the shoulder 100 forming the end of the connecting portion so as not to compromise the seal between the vial and the holding chamber. The slits 87 permit radial collapsing of the connecting portion of the cap, relaxing the material about the rib 92 so that the rib can position itself beneath the overhang of the seal on the neck of the vial.

The shield cap 14 is fully seated on the vial when the shoulder 100 defined by a radial offset 102 between the body 80 and the enlarged diameter connecting portion 85, abuts the facing surface 104 of seal 42. With the cap and vial in the described relative relationship, the shoulder 94 on the rib 92 axially intersects a rounded portion 106 on the corner of the rim 48.

To further secure the shield cap and vial, a cylindrical locking ring 108 is provided and has a radially inturned flange ring portion 109 which guides the ring 108 axially along the body and abuts the offset 102 to establish the fully seated ring position. The ring 108 has a main, cylindrical portion 110 with an inside diameter slightly less than the diameter of the outside surface 112 of the connecting portion 85 of the shield cap with the connecting portion positioned over the vial neck.

The locking ring is brought into axial overlapping relationship with the connecting portion 85. As this occurs, the connecting portion of the cap is compressed radially, when action is accommodated by the slits 87. With the ring in a fully seated position, the rib 92 is forced against the neck of the vial beyond the rounded portion 106 which tends to stretch the connecting portion 85 and closely captures the combined thickness of the seal 42 and the stopper top 36 to still further enhance the seal therebetween. Separation of the cap and vial is precluded as long as the compression locking ring 108 is in position around the connecting portion. A shoulder 113 is integrally molded on the syringe end 86 of the shield cap and is intended to retain the locking ring 108 on the shield cap. During assembly the flange 109 on the locking ring is forced over the shoulder 113. Once the flange 109 is deflected over the shoulder it will return to its original dimension.

The cap and locking ring 108 are preferably made from a moldable material that is deformable sufficiently to facilitate the aforementioned connection between the cap and vial. The material should be resilient enough to maintain a leakproof seal at the point of abutment between the shoulder 100 defined by the offset and the cap surface 104. Further, the material should be capable of establishing a seal about a penetrating cannula. The material should self-seal the rupture made by the cannula with the cannula withdrawn. The significance of this particular feature is elaborated below.

The syringe end 18 of the shield cap 14 has an integral, truncated, parabolic shaped internal seal portion 88, offset axially into the chamber 82 and defining a cavity 120 opening away from the vial end for accepting the leading portion of the needle and syringe. A sealing member 132 forms the truncated part of the seal portion 88.

The cavity 120 is defined primarily by the inner surface 122 of the parabolic portion 88. The inner surface 122 is shaped to provide clearance between the hub 22 of the needle. An enlarged cylindrical recess 124 defines the entrance to the cavity 120 to accept a portion of the cylindrical outer surface 128 of the sleeve of the Luer-lock connector on the syringe. The seal portion 88 defines one wall of the holding chamber 82 with another wall being the cylindrical body 80. One end of the holding chamber is defined by the end of the shield cap with the other end being defined by the end of the vial as it is sealed to the shield cap.

The walls of the recess 124 and cavity 120 cooperatively guide the cannula, syringe hub and Luer-lock sleeve 65 into a fully seated position in the cap. The relationship between the shield cap and the hub 22 makes it possible for the portion 88 of the shield cap to grip the hub 22 whereupon twisting of the syringe relative to the shield cap will assure a firm lock between the hub and syringe. Ribs 129 formed on the surface 122 of portion 88 enhance the gripping of the hub.

The vial package, including the shield cap and vial, can be sold as an assembled unit. To prevent contamination of the cavity 120, a sterile, protective sealing sheet 130 is used to cover the free edge 126 of the cap and is bonded thereto as by the use of an adhesive. The end of the shield cap can be closed and sealed by a tethered flip top configuration of the type shown in FIG. 11.

The operation of the device is as follows. Initially the sheet 130 is peeled off the shield cap. A syringe 56 filled with medicament and with the cannula of the needle unsheathed has the cannula 20 introduced through the cavity 120 and penetrates the sealing member 132. The cannula is directed through the holding chamber 82 and pierces the septum 54 to establish communication between the vial chamber 50 and the syringe reservoir 58. The hub 22 and the Luer-lock sleeve 65 is respectively in the cavity 120 and recess 124 with the Luer-lock sleeve bottomed on the abutting surface between the cavity 120 and recess 124.

Upon depressing the plunger to force the fluid from the reservoir into the vial, pressure is developed in the vial, some of which may aspirate past the cannula into the holding chamber 82. The vial package 10 with the inserted syringe is then shaken to mix the medicaments. Upon completing the mix, the plunger is withdrawn to fill the reservoir 58 with the reconstituted medicament. As the cannula is withdrawn, aspirating of the mixture may occur past the outside of the cannula and into the holding chamber. Upon withdrawal of the cannula, residual pressure may still exist in the vial, which may be substantial if the volume of solution that was introduced is not entirely withdrawn or if a buildup of gas occurs in the vial. At this point, some of the remaining solution under pressure may aspirate into the holding chamber through the puncture 78 in the stopper. All asperated solution is completely captured in the holding chamber 82.

The holding chamber 82 can also be used to expel air bubbles entrained in the solution that is withdrawn from the vial. To accomplish this, the point 64 of the needle is retained in the holding chamber 82 as depicted in solid lines in FIG. 3. The syringe, shield cap and vial are inverted with the vial uppermost so that the air will accumulate at the needle end of the syringe barrel. The plunger is then depressed to expel a small amount of solution and all of the air bubbles into the holding chamber thereby eliminating the bubbles from the barrel. Thereafter, the needle is withdrawn from the shield cap ready for use on a patient. The shield cap and vial with the accumulated aspirated solution confined positively in the holding chamber can be safely handled and disposed of without contamination of the handlers.

Several modifications to the invention are disclosed in the remaining figures. In FIG. 4, a shield cap 214 is shown assembled with a vial 12 and adaptable for use with a syringe 24. Both the vial and syringe are identical to those disclosed in FIG. 1. The shield cap 214 is formed with a cavity 220 similar in shape and function to cavity 120 in FIG. 1. However, the shield cap 214 is substantially solid along its axial coincidence with the cavity 220 whereas in FIG. 3 the chamber 82 has an annular expansion about the cavity. A bore 217 is provided through the solid portion 219 of the cap to provide a communication path between the chamber 220 and a holding chamber 282. The bore 217 guides the cannula to assure coaxial alignment between the syringe and the cap.

The connecting portion 216 of the cap is substantially identical to that in FIGS. 1 and 3. However, rather than the stepped diameter construction between the body 80 and the connecting portion 16 of the cap in FIGS. 1 and 3, the cap in FIG. 4 has a constant diameter along its length. A locking ring 208 operates in the same manner as locking ring 108 in FIGS. 1 and 3, however since the entire inside surface 221 of the ring mates closely with the outside surface 222 of the cap 214, there is no corresponding guiding ring associated with the ring 208.

An additional feature of the construction in FIG. 4 is the provision of a sealing member or sealing layer 224 seated against the end wall 215 of the chamber 282. The sealing member 224 appears as a cylindrical disc and is made preferably from a rubber material that has good self-sealing characteristics. Because the sealing member 224 is provided, the material making up the remainder of the cap need not be self-sealing. The sealing member 224 is fastened to the wall 215 by means of adhesives, ultrasonics or the like.

The shield cap 314 in FIG. 5 is configured similarly to the arrangement in FIG. 4. The primary distinction is that the corresponding solid portion 319 has a curved, reduced diameter middle section 321 which facilitates grasping between a user's fingers. The corners 323 toward the syringe end 318 of the cap are curved for user comfort. The particular cap configuration, in addition to facilitating grasping, also reduces the amount of material required to make up the cap. Substantial cost reduction is realized, particularly when the cap is molded from plastic, as is preferred. A sealing member 324 is seated in the holding chamber 382 against the wall 315.

Another distinction in the FIG. 5 embodiment is the slight modification of the connecting portion 316. With the shield cap 314 in place, a locking ring 308 is assembled. The ring 308 has axially spaced wedge-shaped, annular rings 310,312 extending radially inwardly from the inside ring surface 350. The ring 312 seats in a cooperating groove 330, on the cap 314. Simultaneously, one wall 332 of the ring 310 bears against a bevelled surface 336 adjacent the free edge 338 of the cap.

A further modification to the cap 314 in FIG. 5 is the provision of a resilient annular seal 352 in a recess 354 at the syringe end 318 of the cap. The seal 352 readily deforms to the contour of the Luer-lock connector sleeve 365. The seal 352 is primarily for use with units where the syringe is prefilled and is included as a package with the vial and shield cap. The cannula tip 364 will be seated in the stopper 330 with the seal 352 engaging the forward part of the Luer-lock connector sleeve 365. When the device is ready for use, the syringe is pushed toward the shield cap to complete the penetration of the cannula into the vial.

The FIG. 6 embodiment has a shield cap 414 with a cylindrical body 416 having an intermediate partition 418 separating a holding chamber 482 and hub receiving chamber 484, with the latter loosely accepting the entire leading portion of the syringe. The body 416 is formed (molded or the like) of material with sufficient memory that the partition 418 is the sealing member which is punctured by the cannula when the syringe is assembled with shield cap 414. The puncture in the sealing member will seal when the cannula and syringe are separated from the shield cap 414. The body 416 is integral with an enlarged diameter vial end 420 which connects in similar fashion to the vial end 84 in FIGS. 1 and 3 and is surrounded by a compression locking ring 408 like that shown in FIG. 4.

An additional sleeve 424 is provided and telescopingly mates with the body 416. The sleeve 424 defines a rearwardly opening groove 426 at its free end. An O-ring 428 is seated in the groove 426 and seals between the sleeve and a tapered wall 430 at the leading edge of the barrel 56. The O-ring 428 is preferably fixed to both the sleeve and barrel to make a unitary structure therewith.

The sleeve 424 positively guides the syringe relative to the vial with the attached cap 414. Movement of the syringe toward the vial is arrested as the free edge 470 of the hub abuts the partition 418 as shown in phantom.

A problem that is ofttimes encountered during a mixing operation is the build-up of pressure in the vial. While this normally does not occur with the syringe operated by a skilled technician, the pressure build-up is a problem that must be dealt with. To solve this pressure build-up problem, the FIG. 7 adaptation is appropriate.

In FIG. 7, a shield cap is shown at 514 that is substantially the same as that depicted in FIGS. 1 and 3. The structure is modified by providing a bleeder vent at 516 which may be formed integrally with the cap or manufactured as a separate unit to be assembled therewith. The vent 516 comprises a cylindrical conduit 518 which penetrates the wall of the body 580. An enlarged disc-shaped chamber 520 is formed and is in fluid communication with a passage 522 and a passage 524 through a discharge head 526. Within the chamber 520 a filter element is disposed which may be a hydrophobic filter or an appropriate filter for filtering out the medicament aspirated into the holding chamber 582.

The FIG. 7 invention also contemplates the use of a modified form of cannula 530, the details of which are clearly shown in FIGS. 9 and 10. The cannula has an integrally formed, radially inwardly directed, vent channel 532. The channel 532 provides a bleed path with the cannula inserted through the vial septum. The spite of the self-sealing nature of the stopper, the pressure equalizes through the bleed path on opposite sides of the interface with the cannula in place. If the equilibrium pressure is greater than atmospheric pressure, the pressure will release through the vent structure 516, which filters any harmful impurities that might otherwise expel into the environment.

It should be understood that this particular modification of the cannula 532 might be used with the shield caps of the prior embodiments. In most operations however, the holding chamber 82,282,382,482 are of sufficient volume to allow pressure equalization on opposite sides of the stopper.

Figure 11:
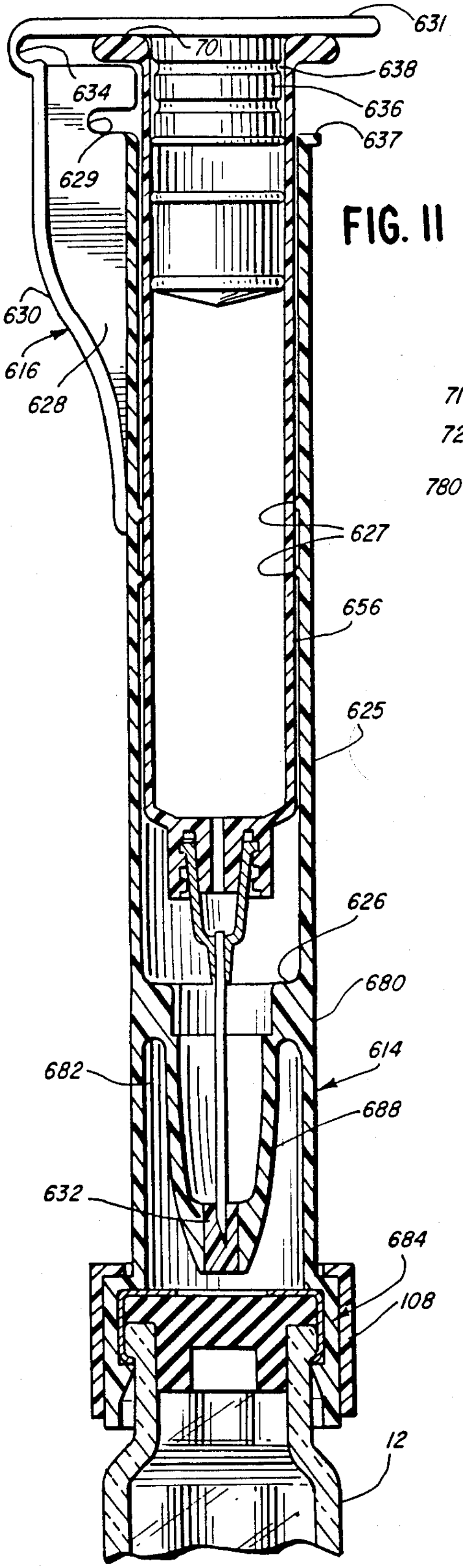
FIG. 11 is a sectional view of the form of invention shown in FIG. 2 only with the parts assembled together in a stored or shipping condition.

FIGS. 2 and 11 show still another form of shield cap 614 as an integral part of a preloaded syringe apparatus. The syringe cap 614 has a syringe plunger positioning arm 616 for retaining a flange 70 of a preloaded syringe 624 in a predetermined position during shipment and storage without plunger rod 666 attached. Specifically, the shield cap 614 has a slotted vial end portion 684 similar to vial end portion 84 of FIGS. 1 and 3. A seal portion 688 is provided in the cylindrical body 680 and has a sealing member 632 closing the inner end thereof. The seal portion 688, cylindrical body 680 and the sealed end of the vial 12 define the holding chamber 682. The cylindrical body 680 is elongate and extends considerably beyond the end 626 of the seal portion 88 to form a retaining sleeve portion 625 which has spaced inwardly disposed concentric ribs 627. The syringe plunger positioning arm 616 is integrally formed as an extension of one segment of the sleeve portion 625 and has a radially outwardly formed web 628 with a retaining notch 629 near the outer end thereof for holding flange 70 in the syringe activated position. A flange 630 is formed outwardly in both directions from the positioning arm 616 to add stiffness to the arm. A closure 631 is tethered by a web 634 to the arm 616 and has a cylindrical plug 636 projecting from one face thereof. Concentric sealing ribs 638 are formed on the outer surface of the plug.

The vial end 684 is sealingly attached to a vial 12 having a powdered medicament 26 therein by means of the slots 87, segments 89, ring 83 and sleeve ring 108 as described with respect to FIG. 3. A syringe 624 is preloaded with a second medicament in front of the stopper 72 whereupon the syringe with the needle assembly 21 attached thereto is advanced into the open end 640 of the sleeve portion 625 of the seal cap 614 until the end of the needle cannula 20 is embedded in the sealing portion 632. The barrel 656 of the syringe will be sealed in the sleeve portion 625 by the ribs 627 which can be used to maintain the unembedded part of the needle cannula 20 in a sterile condition and to add resistance to relative movement between the sleeve and the syringe. The flange 70 on the syringe barrel is positioned against the tooth 642 on the end of the arm 616 when the end of the needle is properly positioned in the sealing portion 632. The closure 631 is pivoted to seat the plug 636 in the end of the syringe barrel and holds plunger 72 in position. A plunger rod 66 is taped or otherwise secured or attached to the assembly during storage and shipment.

To prearm the assembly prior to patient use, the closure 631 is pivoted to remove the plug from the syringe barrel. The plunger rod 666 is threaded (or otherwise connected) to the plunger 72. The arm 616 is urged radially outward to clear the flange 70 whereupon the syringe barrel and needle are urged forward to penetrate the needle through seal 632 and into and through seal 54 of the vial. The flange 70 will seat in the notch 629 and will hit syringe flange stop 637 whereupon the assembly is prearmed.

The medicaments are mixed and the syringe is removed from the sleeve portion 625 ready for injection following the same techniques as described heretofore in reverse order.

Figure 12:
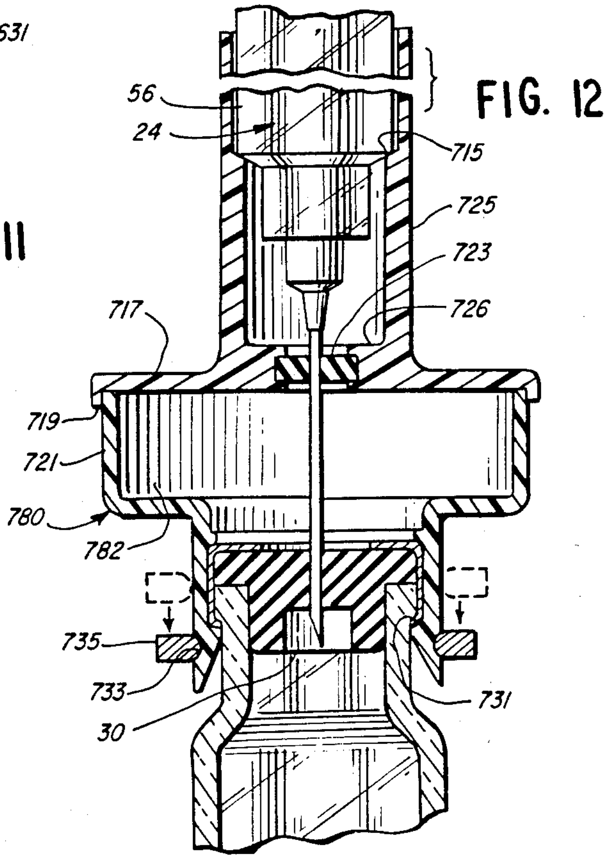
FIG. 12 is a sectional view similar to FIG. 3 with a seventh type of shield cap according to the present invention.

FIG. 12 illustrates an assembly wherein the holding chamber 782 is enlarged to provide an enlarged expansion chamber for the aspirating medicaments. The shield cap assembly 714 has a sleeve portion 725 for receiving the barrel 56 of the syringe 24 and includes a shoulder 715 serving as a stop for the syringe barrel. A flange 717 flares outward of the sleeve portion and has a downturned edge 719 sealed against a wall 721 of a body 780. The body 780 has a cylindrical hub 723 axially aligned with the sleeve portion 725. A rib 726 is formed internally of the one end of the sleeve portion which rib supports a self-sealing puncturable seal 727. The cylindrical hub 723 has a tapered exposed end 729 which terminates in an inturned shoulder 731 which seats behind the seal end 42 of a vial 12. A groove 733 is formed around the outer face of the hub 723 in which a sliding ring 735 seats to hold the shield cap 714 assembled in sealing relationship on the vial.

The syringe 24 is inserted in the sleeve 725 with the needle penetrating through the seal 727 and through the seal 30 in the vial. The medicaments are mixed, the aspirated medicament is trapped in the expansion chamber 782 as described hereinabove.

Figure 13:
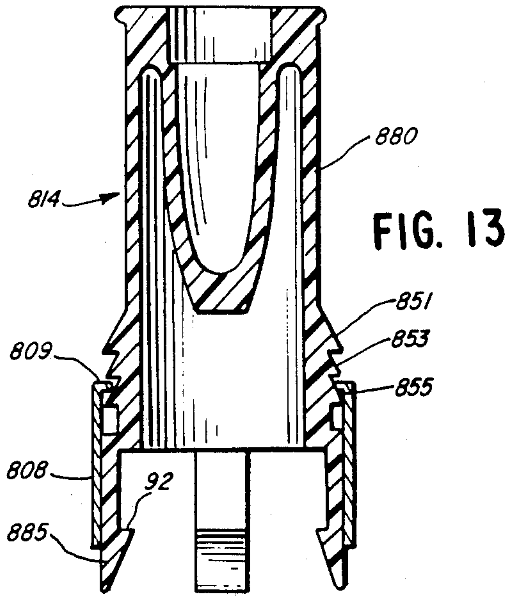
FIG. 13 is a sectional view of a modified form of connection between a shield cap and a vial.

FIG. 13 illustrates a shield cap assembly 814 all as described above with respect to FIGS. 1 and 3 with the addition of an improved positive structure for locking the shield cap to the vial against removal. The vial end 884 has plural axially spaced rows of notches 851,853,855 which may be continuous about the shield cap or may be short circumferential segments. The notches are formed on the cylindrical body 880 axially of the connecting portion 885. The locking ring 808 encircles the cylindrical body and has an inturned flange 809. The diameter of the inner edge of the flange 809 is slightly larger than the outside diameter of the cylindrical body 880 but is smaller in diameter than the outer end portions of the notches 851,853,855. With the connecting portion 885 of the shield cap assembled over the end of a vial 12, the inturned ribs 92 seat beneath the enlarged head on the vial. The locking ring 808 is slid axially over the connecting portion 885 with the flange 809 snapping over successive notches 851,853 and possibly 855 until the shield cap is securely locked on the vial. The flange 809 on the ring 808 once past notches 851,853,855 cannot be backed past any one of said notches, thus locking the shield cap permanently to the vial.

It is of course understood that the locking arrangement for the shield cap of FIG. 13 could be used with the shield cap of FIGS. 1 through 12 and vice versa. Also the sleeve portion 625 and retaining arm 616 of FIG. 11 could be used with the shield cap of FIGS. 1–10, 12 and 13. Various combinations of the novel features shown and described are within the scope of the invention herein disclosed. Other methods of securing the vial may be used and we are not limiting the device to this method.

Figure 14:
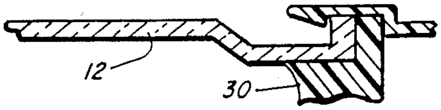
FIG. 14 is a partial sectional view of another modified form of connection between a shield cap and a vial.

In the preloaded form of FIGS. 2 and 11, it may not be necessary to seal the vial with the ring seal 108, but the shield cap can be made of a more rigid material in order that it can be jam fitted over the vial neck and vial stopper to cause a perfect seal with or without the use of the aluminum band. In this instance, it may be necessary to have a more penetrable seal 632, (see FIGS. 14 and 11).

The compression ring seal 108 can be elongated toward the syringe end so as to allow safety to the user in the event that the cannula mistakenly penetrates the wall of the shield cap 14,214,314,414,514,614.

FIGS. 15–20 relate to a vial package wherein a holding chamber is defined at least partially within the vial as opposed to definition external to the septum as described in the above forms.

Figures 15, 16, 17, 18, 19, 20, 21:
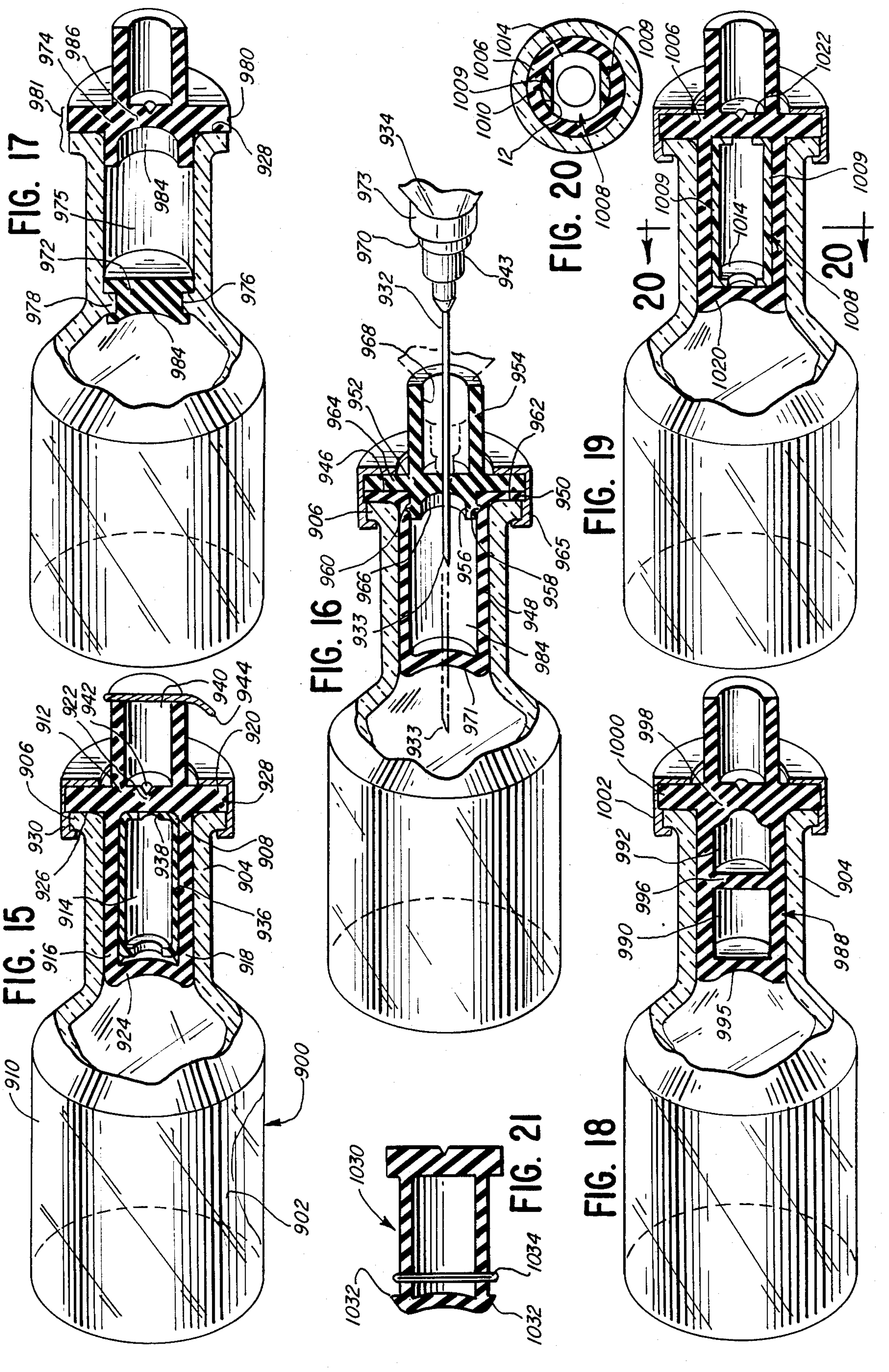
FIG. 15 is a partial sectional view of an alternative form of vial package embodying the invention with a modified vial and a resilient insert.
FIG. 16 is a view similar to that in FIG. 15 with a modified insert and the vial and package shown in relationship to a syringe in communication with a holding chamber in the vial, a second position of the syringe being shown fully seated in phantom.
FIG. 17 is a view similar to that in FIGS. 15 and 16 showing an alternative insert form and a modified vial.
FIG. 18 is a view similar to that in FIGS. 15–17 with a further alternative form for the insert.
FIG. 19 is a view similar to that in FIGS. 15–18 with a still further alternative form for the insert.
FIG. 20 is a sectional view of the neck of the vial with the insert in place along line 20—20 of FIG. 19.
FIG. 21 is an elevational view, partly in section, illustrating a still further alternative form for the insert.

Referring initially to FIG. 15, a vial at 900 is shown comprising a body 902 gradually converging into a reduced diameter, elongate neck 904. The neck 904 has an enlargement 906 adjacent an opening 908 through which communication can be established with the inside of the vial. The body 902 of the vial defines an internal mixing chamber 910 which normally contains one constituent of a multi-component medicament.

The invention resides primarily in the provision of an insert 912 which defines a holding chamber 914 at least partially interiorly of the vial. The insert 912 has a cup-shaped or cylindrical body 916 which fits closely within the cylindrical inside surface 918 of the neck. Preferably, the body 916 is made of a deformable rubber material that compresses and sealingly engages upon being press fit within the vial neck. Integrally formed with the body is an enlarged head 920 which includes an end wall 922 closing one end of the holding chamber 914. The wall 922 of the head 920 and an end wall 924 at the opposite end of the body 916 cooperatively define and axially seal the holding chamber 914.

In assembling the insert, one merely presses the insert into the vial neck through the opening 908. A shoulder 926, defined by the enlarged head 920, abuts an exposed surface 928 on the vial neck to arrest movement of the insert at a predetermined position relative to the vial. A deformable metal sealing cap 930 captively engages the enlargement 906 on the vial neck and the enlarged head 920 associated with the insert to seal the insert on the vial. Because some of the rigidity of the material of the insert 912 may be compromised in making it self-sealing, a more rigid plastic liner 936 is situated internally of the holding chamber. The liner substantially conforms to the shape of the outer cylindrical walls of the holding chamber and is provided with enlarged apertures 938 at each end so that penetration of the end walls 922, 924 by the cannula is unimpeded.

It is also contemplated that a luer seal 940 be formed integrally with the head 920 for cooperation with the luer connector 943 (FIG. 16) on a syringe 934. To assure that the alignment of a cannula 932 on the syringe 934 and the vial package is proper, and to reduce the force necessary to penetrate the end wall 922, a converging notch 942 is formed in the end wall 922 of the insert. This notch 942 tends to guide the cannula properly into association with the insert.

In operation, the cannula 932 (FIG. 16) associated with the syringe 934 (FIG. 16) extends from right to left to initially rupture the end wall 922 and in turn the end wall 924 of the insert. This operation establishes communication between the mixing chamber 910 and the barrel (not shown) associated with the syringe. The mixing operation is performed as previously described.

After the medicaments are mixed and the mixture is drawn into the barrel, the cannula is removed from the vial to the point where the end of the cannula resides in the holding chamber 914. Fluid in the mixing chamber under pressure may aspirate through the rupture in the insert formed by the cannula into the holding chamber 914 and is there confined. Air in the mixture in the barrel of the syringe is aspirated into the holding chamber 914. The aspirated mixture is confined in the holding chamber so as not to contaminate the individuals or the facilities in and around the area where the mixing and use of the medicament takes place.

The resulting package as seen in FIG. 15 can be placed in a sterile container or, alternatively, the admitting end of the luer seal 940 can be sealed by a sterile strip 944 or the like. To use the package, the sterile strip 944 is removed and a syringe cannula inserted as previously described. The package is thus saleable as a prefabricated unit.

FIG. 16 shows a vial that is identical to that in FIGS. 15, 18 and 19. The modification lies in the insert at 946 which comprises two separate elements. A cup-shaped cylindrical body 948 seats internally of the vial neck and has an enlarged rim 950 for abutment with the exposed surface 928 of the vial. A stopper 952 with an integral luer seal 954 has a cylindrical extension 956 which snap fits interiorly of the body 948. The neck of the body 948 has a peripheral groove 958 which accepts a complementary annular bead 960 on the extension 956. The bead 960 seats firmly in the groove 958 simultaneously as a shoulder 962 defined by an enlarged flange 964 abuts the rim 950 of the body 948. In like manner, a metal seal cap 965 can be deformed about the intimately engaged vial neck enlargement 906, the rim 928 and the head 964 of the stopper 952 to fix the relationship of those elements.

To facilitate penetration by the cannula 932 on a syringe 934 a partial bore or cavity 966 is made in the stopper to reduce the effective thickness that is penetrated by the cannula at the same time allowing sufficient axial extension to provide a firm engagement between the bead and groove.

FIG. 16 shows the relationship between the luer seal 954 and the end 943 of the syringe. The syringe end 943 has a stepped construction and a cylindrical chamber 968 in the luer seat is internally dimensioned to closely accept the peripheral surface largest diameter portion 970. It is contemplated that the forward end portion of the large diameter portion 970 of the syringe seats just inside the luer seal 954 with the point 933 of the needle or cannula 932 just touching the closed end 971 of the body 948. An appropriate spacer 973 may be positioned around portion 970 of the syringe to form a shoulder for holding the needle point 933 against or sealed in the closed end 980. When the device is ready for mixing, the spacer 973 is removed and the syringe is pushed forward to penetrate the needle point into the vial where the mixing takes place. After mixing the syringe and cannula are backed into the solid line position for aspirating into the closed holding chamber 984.

In FIG. 17, an insert comprises two unconnected pieces, one a disk-shaped plug 972 and the other a separate stopper 974. The plug and stopper confine an axial length of the vial neck and cooperate with the inside surface of the vial to define a holding chamber 975 rather than entirely enclosing the holding chamber as the inserts in the FIGS. 15 and 16 embodiments. The disk-shaped plug 972 has a groove 976 which could be squared and which accepts a complementary bead 978, integrally formed with the vial.

The stopper 974 is formed substantially as the stopper in FIG. 16. An enlarged head 980 abuts directly against the exposed surface 928 of the vial and is maintained by a deformable metal cap 981.

To reduce the effective thickness of the wall 982 of the disk-shaped member 972, a curved indentation 984 is provided. The partial bore 984 in the wall 986 of the stopper reduces its effective thickness.

FIG. 18 shows an insert 988 having one piece-two compartment 990,992 holding chamber 993. The insert 988 seats in the vial neck 904 and has a cylindrical body 994 with a closed inner end 995, a partition 996, a closed outer end 998, an enlarged head portion 1000 and a luer seal 1001. A metal cap 1002 seals the head portion 1000 to the end of the vial. The inner end 995 and partition 996 define one compartment 990 and the partition 996 and outer end wall 998 define the second compartment 992. The device is used in the same manner as FIG. 16 except that the vial aspirating through wall 995 and the syringe aspirating both take place in compartment 990 of the holding chamber with the second compartment 992 acting as a safety chamber in the event aspirated medicament leaks past the partition 996. It is also possible to let the first compartment 990 catch aspirated medicament from the vial with the aspiration of the syringe taking place into the second compartment 992.

A still further embodiment of the invention is shown in FIGS. 19 and 20. The insert 1006 is substantially the same as that disclosed in FIG. 15. Instead of a continuous liner as in FIG. 15, a rectangular liner 1008 has spaced and shaped sides 1009 as most clearly seen in FIG. 20. The peripheral surface 1010 of the sides 1009 are contoured to closely mate with the inside surface 1012 of the insert 1006. The liner is intimately engaged with the ends 1020, 1022 at the insert at its axial ends 1014, 1016. The ends 1014, 1016 have openings 1018 for free passage of the cannula 932 of the syringe. The sides of the liner could be rod shaped so as to hold the ends 1014, 1016 spaced apart and in supporting relationship with the ends 1020, 1022 of insert. The liner holds the ends 1020, 1022 of the insert 1006 apart to define a holding chamber 1024 in the insert for use with the syringe 934 as described above.

It should be understood that the foregoing detailed description was made for purposes of identifying the structue and operation of the invention, with no unnecessary limitations to be understood therefrom.

The final embodiment of the invention is shown in FIG. 21. The insert 1030 shown in this figure is particularly useful when it is desired to produce a freeze-dried substance in a vial such as that shown in the preceding figures. The insert 1030 includes one or more tabs 1032 which are utilized to pre-position the insert 1030 in the neck of a vial and which provide a small space between the insert and the vial neck to in turn provide a route for escape of lyophilized gas produced during the freeze-drying process. A seal ring 1034 is also provided which allows the escape of lyophilized gas from the vial but which seals against subsequent escape of medicament under pressure following admixture of the freeze-dried medicament and diluent and withdrawal of a syringe cannula.

The embodiment of FIG. 21 is further characterized by the absence of a luer seal. It should be noted that in any of the above-disclosed embodiments, the luer seal can be dispensed with, if desired.

It is also possible to adapt any of the above embodiments for use with standard, presently-available vials not having an elongate neck, in which case the holding chamber described previously would be substantially reduced in size.

We claim:

1. In combination: a vial having a mixing chamber and a neck for containing a fluid supply and an opening in the neck for gaining access to the mixing chamber;
 - an insert extendible through said opening and providing a sealed holding chamber at least partially within said neck; and
 - means for securing the insert to the vial to prevent separation therefrom and so that the insert seals the vial against the escape of fluid from the mixing chamber,
 - whereby the cannula of a syringe can be extended through the insert to establish fluid communication with the mixing chamber, and upon removing said cannula from the insert, aspirating fluid from the mixing chamber and from the syringe is substantially confined in the holding chamber to prevent exposure by the user to the fluid.

2. The combination according to claim 1 wherein said means connect the insert to the vial neck.

3. The combination according to claim 1 wherein said insert has an enlarged head that bears against the head of the vial to prevent passage of the insert through the opening.

4. The combination according to claim 1 wherein said neck extends between a body defining the mixing chamber and the vial head and said neck has a cylindrical internal passage and said insert conforms to and fits closely within said passage.

5. The combination according to claim 1 wherein said insert includes a luer seal for mating with a syringe.

6. The combination according to claim 3 wherein a cap is deformed over the enlarged insert head and vial head and captively maintains the enlarged insert head against the vial head.

7. The combination according to claim 4 wherein said insert is formed from a resilient material and a liner is fit within the holding chamber to maintain the shape of the holding chamber.

8. The combination according to claim 5 wherein said insert and luer seal are integrally formed from a rubber material.

9. The combination according to claim 7 wherein said liner is made from a rigid plastic.

10. An improved medicinal apparatus for containing a fluid supply comprising:
 - a vial having a body providing a primary mixing chamber and an elongate neck integral with the body and providing a cylindrical internal passage and an opening at an end of the neck;
 - first means providing a sealed holding chamber at least partially within the vial neck,
 - said first means having spaced walls and sealingly engageable within the vial neck; and
 - second means for securing the first means with the vial neck,
 - whereby a cannula on a syringe is extendible through said spaced walls to establish communication with the primary mixing chamber and whereby said holding chamber substantially confines fluid aspirating from the primary mixing chamber and from said syringe upon partial withdrawal of the cannula from the vial to prevent exposure by the user to the fluid.

11. The improved medicinal apparatus of claim 10 wherein said first means comprises a disk-shaped element having a cross section conforming to the internal passage and defining one of the spaced walls and a separate stopper seals the opening at the end of the vial neck and defines the other of said spaced walls.

12. The improved medicinal apparatus of claim 10 wherein said first means comprise an enclosed cylindrical member, an enlarged head on the first means abuts the vial neck and said second means comprises a cap deformed about the enlarged head and vial neck to captively maintain the first means in fixed relationship to the vial.

13. The improved medicinal apparatus of claim 10 wherein said first means comprises a cylindrical member with peripheral surface and an enlarged rim which bears against said neck with the first means in place in the vial and said peripheral surface is interrupted to give flexibility to assist in assembling the cylindrical member in the vial neck.

14. The improved medicinal apparatus of claim 10 wherein said first means comprises a cylindrically shaped member conforming to the internal passage with a closed end defining one of the spaced walls and an open end, said first means having an enlarged rim adjacent the open end, said first means further comprising a stopper fit sealingly in the open end of the cylindrically shaped member and defining the other of the spaced walls.

15. The improved medicinal apparatus of claim 11 wherein said disk-shaped element has a peripheral surface and said second means comprises an annular rib extending radially into the internal passage and a cooperating groove on the peripheral surface of the disk-shaped element.

16. The improved medicinal apparatus of claim 14 wherein the stopper has an integrally formed luer seal for accepting a syringe.

17. In combination:
 - a medicinal vial of the type having a mixing chamber, a neck and an opening in the neck; and
 - an insert with a housing having a cup-shaped configuration with a closed end insertable through the opening in the vial neck, an enlarged rim on the housing to abut the head of the vial and arrest insertion of the housing in the vial at a predetermined position, and means for sealing at the end opposite the closed end to provide a sealed holding chamber,
 - said closed end and said sealing means being penetrable by a syringe cannula to establish fluid communication with the mixing chamber, and upon removing said cannula from the insert aspirating fluid from the mixing chamber and from the syringe is substantially confined in the holding chamber to prevent exposure by the user to the fluid.

18. The combination according to claim 17 wherein said sealing means comprises a stopper with an enlarged head to abut the rim which in turn seats on the vial head so that a cap can be applied to captively hold the enlarged head, rim and vial head together.

19. The combination according to claim 17 wherein said sealing means is integrally formed with said rim.

20. The combination according to claim 18 wherein a luer seal is formed integrally with the stopper to accept a syringe.

* * * * *